US009286944B2

(12) United States Patent
Kirenko et al.

(10) Patent No.: US 9,286,944 B2
(45) Date of Patent: Mar. 15, 2016

(54) METHODS AND SYSTEMS FOR PROVIDING A COMBINATION OF MEDIA DATA AND METADATA

(75) Inventors: Ihor Olehovych Kirenko, Eindhoven (NL); Maarten Peter Bodlaender, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 446 days.

(21) Appl. No.: 13/504,496

(22) PCT Filed: Nov. 1, 2010

(86) PCT No.: PCT/IB2010/054928
§ 371 (c)(1),
(2), (4) Date: Apr. 27, 2012

(87) PCT Pub. No.: WO2011/055288
PCT Pub. Date: May 12, 2011

(65) Prior Publication Data
US 2012/0212631 A1 Aug. 23, 2012

(30) Foreign Application Priority Data

Nov. 4, 2009 (EP) .................................. 09175006

(51) Int. Cl.
*H04N 19/115* (2014.01)
*H04N 19/186* (2014.01)
(Continued)

(52) U.S. Cl.
CPC .......... *G11B 27/3027* (2013.01); *A61B 5/0059* (2013.01); *A61B 5/7232* (2013.01); *H04N 19/115* (2014.11); *H04N 19/17* (2014.11); *H04N 19/186* (2014.11)

(58) Field of Classification Search
None
See application file for complete search history.

(56) References Cited

U.S. PATENT DOCUMENTS 5,754,675 A * 5/1998 Valadier ........................ 382/115
8,005,776 B2 * 8/2011 Fithian et al. ................... 706/46
(Continued)

FOREIGN PATENT DOCUMENTS

CN 101316552 A 12/2008
JP 2001346768 A 12/2001
(Continued)

OTHER PUBLICATIONS

Brezeale et al., "Automatic Video Classification: A Survey of Literature," IEEE Trans. on Systems, Man and Cybernetics, Part C: Applications and Review, vol. 38, No. 3, May 2008, pp. 416-430.*
(Continued)

*Primary Examiner* — Jay Patel
*Assistant Examiner* — Reza Aghevli
(74) *Attorney, Agent, or Firm* — Sherry Womack Austin

(57) ABSTRACT

A method of providing a combination of video data (37) and metadata (34) includes obtaining a sequence (23) of images captured by a video camera (5). At least one signal (24) is extracted from the sequence (23) of images, wherein each extracted signal (24) characterizes local temporal variations in at least one of light intensity and color. At least one video compression technique is applied on image data of images from the sequence (23) to obtain compressed video data (37). The extracted signals (24) are extracted from images in a state prior to the application of the at least one compression technique to image data from those images. The compressed video data (37) is provided with metadata (34) for characterizing at least one process in a subject represented in at least part of the images, which process causes local temporal variations in at least one of color and intensity of light captured from the subject. The metadata (34) is at least based on at least one of the extracted signals (24).

19 Claims, 5 Drawing Sheets

(51) Int. Cl.
    *G11B 27/30*      (2006.01)
    *A61B 5/00*       (2006.01)
    *H04N 19/17*      (2014.01)

(56) References Cited

U.S. PATENT DOCUMENTS

| 8,270,303 | B2* | 9/2012 | Sauerwein et al. | 370/240 |
|---|---|---|---|---|
| 2009/0087042 | A1* | 4/2009 | Steinberg et al. | 382/118 |
| 2009/0132441 | A1* | 5/2009 | Muller et al. | 706/11 |
| 2009/0161994 | A1* | 6/2009 | Sauerwein et al. | 382/313 |
| 2009/0192961 | A1* | 7/2009 | Fithian et al. | 706/46 |

FOREIGN PATENT DOCUMENTS

| JP | 2005218507 A | 8/2005 |
|---|---|---|
| JP | 2008142150 A | 6/2008 |
| JP | 2009106680 A | 5/2009 |

OTHER PUBLICATIONS

Jean-Baptiste et al., "MPEG-7 Descriptor Integration for On-line Video Surveillance Interface," IEEE Int'l. Conf. on Systems, Man and Cybernetics, Oct. 2007, pp. 308-312.

Annesley et al., "Evaluation of MPEG7 Color Descriptors for Visual Surveillance Retrieval," Proc. of 2nd Joint IEEE Int'l. Workshop on VS-PETS, Beijing, China, Oct. 2005, pp. 105-112.*

Murphy et al., "Tracking of Multiple Objects using MOPEG-7 Visual Standards," IEEE Int'l. Conf. on Computational Intelligence and Multimedia Applications, 2007, pp. 267-271.*

Brezeale et al: "Automatic Video Classification: A Survey of the Literature"; IEEE Transactions on Systems, Man and Cybernetics—Part C: Applications and Reviews, vol. 38, No. 3, May 2008, pp. 416-430.

Jean-Baptiste et al: "MPEG-7 Descriptor Integration for On-Line Video Surveillance Interface"; IEEE International Conference on Systems, Man and Cybernetics, Oct. 2007, pp. 308-312.

Annesley et al: "Evaluation of MPEG7 Color Descriptors for Visual Surveillance Retrieval"; Proceedings 2nd Joint IEEE International Workshop on VS-PETS, Beijing, China, Oct. 2005, pp. 105-112.

Murthy et al: "Tracking of Multiple Objects Using MPEG-7 Visual Standards"; IEEE International Conference on Computational Intelligence and Multimedia Applications, 2007, pp. 267-271.

Regazzoni et al: "Multisensor Surveillance Systems Based on Image and Video Data"; IEEE International Conference on Image Processing, Sep. 2002, vol. 1, pp. 497-500.

"Overvew of the MPEG-7 Standard (Version 5)"; International Organization for Standardisation, ITU Study Group 16—Video Coding Experts Group—ISO/IEC MPEG & ITU-T VCEG (ISO/IEC JTC1/SC29/WG11 and ITU-T SG16 Q6) No. M7813, Nov. 2001, 72 Page Document.

Viola et al: "Robust Real-Time Object Detection"; Second International Workshop on Statistical and Computational Theories of Vision-Modeling, Learning, Computing, and Sampling; Vancouver, Canada, Jul. 13, 2001, pp. 1-25.

"MPEG-7 Visual Part of Experimentation Model Version 10.0"; ITU Study Group 16—Video Coding Experts Group—ISO/IEC MPEG & ITU-T VCEG (ISO/IEC JTC1/SC29/WG11 and ITU-T SG16 Q6), No. N4063, Mar. 2001, 83 Page Document.

De Haan et al: "True-Motion Estimation With 3-D Recursive Search Block Matching"; IEEE Transactions on Circuits and Systems for Video Technology, vol. 3., No. 5, Oct. 1993, pp. 368-379.

Cupillard et al: "Tracking Groups of People for Video Surveillance"; Chapter 7 of Book "Video-Based Surveillance Systems: Computer Vision and Distributed Processing"; Kluwer Academic Publishers, Jan. 2002, pp. 89-100.

\* cited by examiner

US 9,286,944 B2

METHODS AND SYSTEMS FOR PROVIDING A COMBINATION OF MEDIA DATA AND METADATA

FIELD OF THE INVENTION

The invention relates to a method of providing a combination of media data and metadata, a system for providing a combination of media data and metadata. The invention also relates to a signal including a combination of compressed video and metadata, wherein the compressed video is obtainable by applying at least one video compression technique on image data of images from a sequence of images. The invention further relates to a method of processing such a signal, a system for processing such a signal, and a computer program.

BACKGROUND OF THE INVENTION

US 2009/0192961 A1 describes a system for adapting the bit rate of a media stream based on user interest. Collected biometric data can be used to determine a user's emotional interest and optionally adjust the bit rate of media and/or present navigation options to one or more selected portion of the stored media. Biometric data can include heart rate, respiratory rate, galvanic skin response, pupil dilation, blood pressure, body temperature and the like. Biometrics can be collected from sensors, which can include electrodermal sensors, microphones, thermometers, accelerometers and the like. In an embodiment, changes in user interest can trigger a variable bit rate encoder to adjust the bit rate processing of captured audio/video based on configuration options. For example, a digital camera can obtain biometric data during picture capture. When user interest is detected as high, the image resolution and megapixel count can be increased, storing the picture as a high fidelity image. Collected biometric data can be stored as metadata in the images for use in playback and navigation.

A problem of the known system is that it is limited to the biometric data that can be obtained at the time of capture. Only the biometric data characterizing the person attached to the sensor is obtained. Additional biometric sensors of the described type are required for each additional person, and each person must co-operate.

SUMMARY OF THE INVENTION

It is desirable to provide a method, system, signal and computer program of the types referred to above that allow for the efficient provision of video data with metadata characterizing processes in subjects represented in the video.

To this end, according to a first aspect, there is provided a method of providing a combination of video data and metadata, including:
obtaining a sequence of images captured by a video camera;
extracting at least one signal from the sequence of images, wherein each extracted signal characterizes local temporal variations in at least one of light intensity and color;
applying at least one video compression technique on image data of images from the sequence to obtain compressed video data,
wherein at least one of the signals is extracted from images in a state prior to the application of the at least one compression technique to image data from those images; and
providing the compressed video data with metadata for characterizing at least one process in a subject represented in at least part of the images,
which process causes local temporal variations in at least one of color and intensity of light captured from the subject,
wherein the metadata is at least based on at least one of the extracted signals.

A subject represented in a sequence of images will generally be a living subject, but may be an inanimate object. A process causing local temporal variations in at least one of light intensity and color will generally be an internal process independent of any movement of any externally visible part of the subject. It may, however, be a process of internal movement (e.g. rotation or reciprocal movement of a part of a subject relative to a reference frame fixed to the subject) of a visible part of the subject in some applications. In the case of a living subject and an internal process, the extracted signals carry information corresponding to at least one biometrical signal.

By providing compressed video data, the method is relatively efficient. Because compressed video data, in particular compressed video data obtained using predictive coding is generally no longer suitable for extracting signals representative of local temporal variations in at least one of light intensity and color, which might be used to obtain data characterizing at least one biological phenomenon in a subject represented in the image, the method provides metadata that corresponds to or is suitable for use in obtaining such data characterizing a biological phenomenon. The method is based on the extraction of at least one signal from the sequence of images prior to compression, so that the small-scale variations in intensity and/or color that are caused by processes in a subject represented in at least part of the images are still represented in the extracted signals. By being based on such extracted signals, the method can be used to obtain data characterizing multiple persons represented in the sequence of images, namely by extracting multiple signals, without having to provide additional sensors. The method is also essentially independent of living subjects' willingness to co-operate, since no sensors placed on the body are required. The method is suitable e.g. in surveillance applications to provide biometric data in combination with compressed video. The biometric data can be used to identify portions of the compressed video requiring closer scrutiny. Because the video is compressed, a data transmission network with a relatively low capacity can be used for collecting video and metadata from camera systems. The system can easily be arranged to enable short-term responses to events signaled by the metadata by persons having access to the compressed video to determine the nature of the event.

An embodiment of the method includes adapting the application of the at least one compression technique in dependence on an outcome of an analysis of data at least based on obtained parts of at least one of the extracted signals.

This embodiment can be used to provide a solution to the problem that more metadata may be required if there are more persons represented in the sequence of images and biometric data relating to each of them individually is to be recoverable from the metadata. The amount of included metadata can be varied according to need (amount of information) whilst keeping the total amount of data (compressed video and metadata) within bounds. Alternatively or additionally, this embodiment can be used to apply more or less compression on certain spatial parts of the sequence of images, depending on whether those parts represents subjects of interest or not. For example, the extracted signals can be used to determine where the faces of living persons represented in the images are located. These spatial parts of the images can be encoded such as to preserve more detail. The same is true where predictive coding is used as part of the compression technique. If it is determined that parameters characterizing the process vary rapidly in time during intervals corresponding to certain sections of the sequence of images, then less interpolation can be applied to encode these sections as part of the compression.

An embodiment of the method includes, whilst obtaining the sequence of images, causing adjustments of parameters of a process of capturing the images using at least one camera in dependence on an outcome of an analysis of data at least based on obtained parts of at least one of the extracted signals.

This embodiment makes it possible to use a relatively cheap camera without generating unreliable data characterizing the processes in a subject represented in the sequence of images. Instead of having to use a high-definition camera, parameters can be adjusted so that the components of the extracted signal or signals carrying the information relating to the process in the subject are more clearly present in the extracted signals. In one variant of this embodiment, parameters affecting the settings of an optical system used to focus light onto a sensor array are adapted. Thus, it is possible to zoom in to capture more information relating to certain parts of a scene represented in the sequence of images. The number of pixels used to create the extracted signal or signals can thus be increased. Alternatively more extracted signals carrying information relating to the same process can be generated, which will then result in a more reliable consensus signal or value characterizing the process in the subject. In another variant, at least one parameter of a system for converting light intensity into discrete pixel values is adjusted in dependence on an outcome of the analysis of the data at least based on obtained parts of at least one of the extracted signals. Examples of such parameters include the gain and discretisation threshold of an image sensor array. In this embodiment, the pixel values carry more reliable information representative of small-scale variations in color or intensity, typically due to internal (especially biological) processes. Other parameters that can be adjusted include exposure time and frame rate (typically parameters of a system for converting light intensity into discrete pixel values, since digital cameras will generally not have mechanical shutters).

In an embodiment, the method is carried out by a processing system included in a camera.

This means that the processing system is included in the same housing as the image sensor array. This embodiment largely avoids the communication of uncompressed video data, and is therefore relatively cheap to implement. In a particular variant, the camera is provided with at least one network interface, so that the combination of video data and metadata is transmittable over a network by the camera itself. This combination is in one embodiment a multiplex of compressed video and a stream of metadata synchronized with the compressed video stream. Suitable cameras (so-called IP cameras) already exist. This variant of the method merely requires them to be suitably configured to carry out the method.

In an embodiment, the metadata includes at least one signal characterizing local temporal variations in at least one of light intensity and color in the sequence of images.

Thus, the metadata includes signals essentially similar to the extracted signals. They may, however, be the result of an operation combining two or more of the extracted signals, e.g. an averaging or clustering operation. In this embodiment, the system providing the combination of metadata and compressed video need not carry out the processing necessary to arrive at accessible information characterizing the processes in the subject in a concise way. This type of processing is carried out by an external system arranged to process the combination of compressed video data and metadata. Accordingly, the type of processing can be varied. Moreover, the system providing the combination of metadata and compressed video can be simpler. One expensive system can process the compressed video data and metadata provided by several cameras, for example.

According to another aspect of the invention, there is provided a system for providing a combination of video data and metadata, including
 at least an interface to a camera for capturing a sequence of images;
 a video data processing system, configured to:
 apply at least one video compression technique on image data of images from the sequence to obtain compressed video data,
 extract at least one signal from the sequence of images, each extracted signal characterizing local temporal variations in at least one of light intensity and color and
 to generate metadata for characterizing at least one process in at least one subject represented in at least part of the images,
 wherein the extracted signals are extracted from images in a state prior to the application of the at least one compression technique to image data from those images and
 wherein the metadata characterizes processes causing local temporal variations in at least one of color and intensity of light captured from the subject and the metadata are at least based on at least one of the extracted signals; and
 an output interface for providing the compressed video data with the metadata.

In an embodiment, the system is configured to carry out a method according to the invention.

According to another aspect of the invention, there is provided a signal including a combination of compressed video and metadata, wherein the compressed video is obtainable by applying at least one video compression technique on image data of images from a sequence of images and the metadata includes at least one signal characterizing local temporal variations in at least one of light intensity and color in the sequence of images.

A system arranged to receive and process the signal can obtain information characterizing processes in subjects represented in the images. Because the metadata includes at least one signal characterizing local temporal variations in at least one of light intensity and color in the sequence of images, various types of such information can be obtained. For example, the extracted signals can be used to determine either the heart rate or the respiration rate of a living subject represented in the images. Only one type of metadata is required for this, namely the extracted signals. One effect is that the signal can be generated by relatively uncomplicated camera systems. Another effect is that it is not necessary to achieve standardization of a large number of different types of metadata (i.e. agreement on codes indicating the variable that a particular numerical value in the metadata represents). One type of metadata is sufficient. In a variant, the metadata will indicate the spatial location to which a particular signal representative of local variations in at least one of light intensity and color pertains.

In an embodiment, the signal is obtainable by executing a method according to the invention.

According to another aspect of the invention, there is provided a method of processing a signal according to the invention, including calculating at least one value of a parameter characterizing at least one process in a subject represented in at least part of the sequence of images, which process causes local temporal variations in at least one of color and intensity of light captured from the subject, using as input at least one of the signals characterizing local temporal variations in at least one of light intensity and color in the sequence of images.

According to a further aspect of the invention, there is provided a system for processing a signal including a combination of compressed video and metadata, including:

an interface for obtaining a signal according to the invention and a data processing system for calculating at least one value of a parameter characterizing at least one process in a subject represented in at least part of the sequence of images, which process causes local temporal variations in at least one of color and intensity of light captured from the subject, using as input at least one of the signals characterizing local temporal variations in at least one of light intensity and color in the sequence of images.

According to yet another aspect of the invention, there is provided a computer program including a set of instructions capable, when incorporated in a machine-readable medium, of causing a system having information processing capabilities to perform a method according to the invention.

BRIEF DESCRIPTION OF THE DRAWINGS

The invention will be described in further detail with reference to the accompanying drawings, in which.

DETAILED DESCRIPTION

Figure 1:
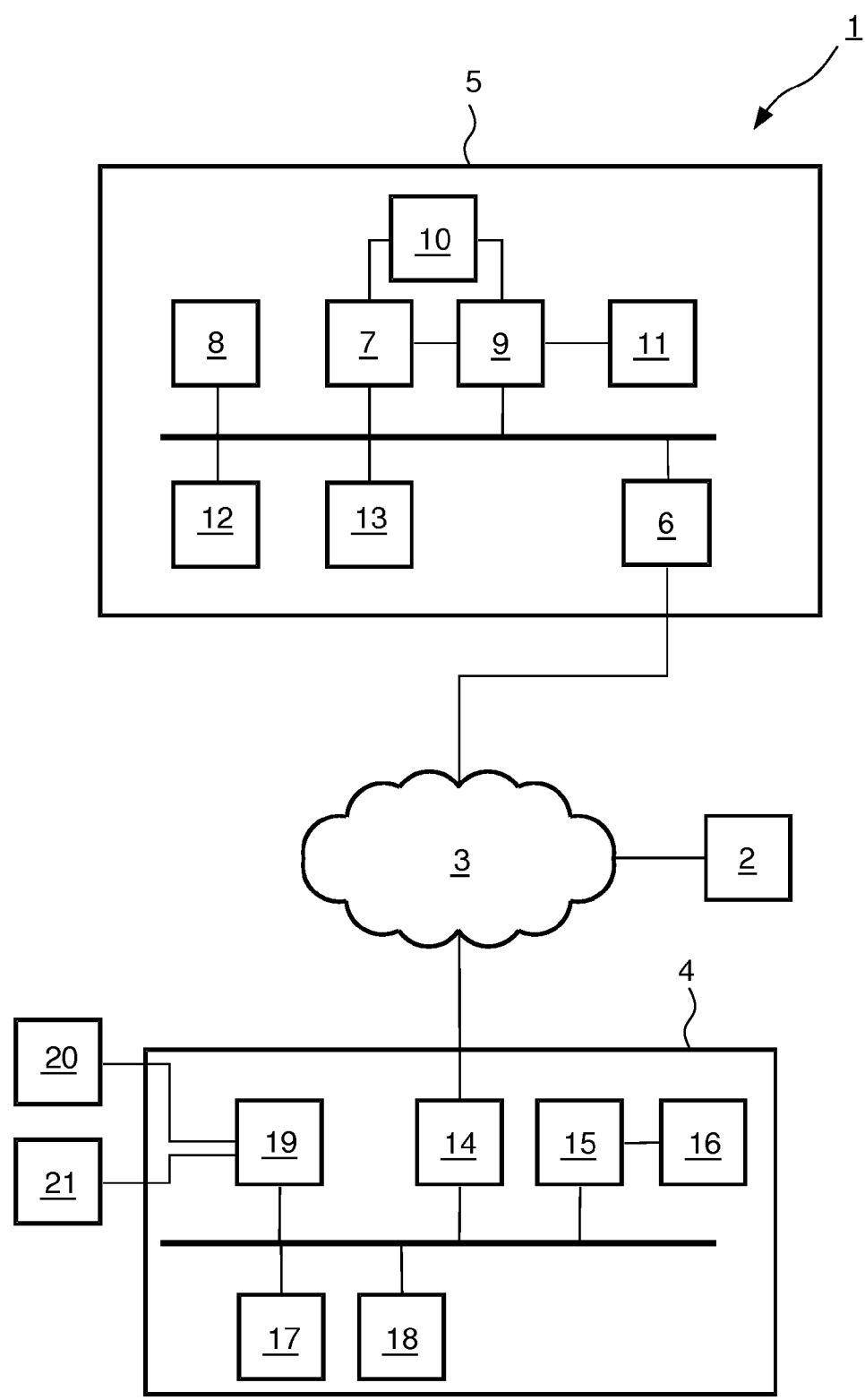
FIG. 1 is a schematic block diagram of a system comprising a camera system for generating a signal combining a compressed video stream with metadata and a system for processing this combined signal.

A system comprising a first and second camera system 1,2, a network 3 and a video signal processing system 4 is used here to explain methods of providing and processing a combination of compressed video data and metadata. In the illustrated embodiment, the first camera system 1 comprises a single camera 5 with a network interface 6. In another embodiment, the first camera system 1 comprises a combination of a computing device and a camera connected thereto, e.g. via a direct link, and operating under the control of the computing device, which also processes raw uncompressed video data to generate a combination of compressed video data and metadata.

The second camera system 2 can have the same build-up as the first camera system 1, and is not illustrated in more detail for this reason.

The camera 5 includes an image sensor array 7, e.g. a CCD or CMOS sensor array of a known type. It further includes an optical system 8 for focusing light from a scene onto the image sensor array 7. The optical system 8 will generally include one or more lenses, filters, a diaphragm and the like, each of which can be adjusted under the control of a camera processor 9. Similarly, the camera processor 9 can set parameters of the image sensor array 7, including integration time, gain, discretisation threshold, etc. It is noted that where reference is made herein to sequence of images, this can include combinations of sequences of images in different color channels. Thus, an image can mean the combination of two or more, e.g. three, image frames, each an array of pixel values representing the captured intensity of light in a particular range of the electromagnetic spectrum. It is further noted that the camera 5 can be arranged to operate in either the visible or the invisible part of the electromagnetic spectrum, or in both. Thus, images can consist of or comprise an array of pixel values representing captured intensities in the infra-red part of the spectrum.

In the illustrated embodiment, a video encoder 10 is provided to compress raw image data, and thereby generate compressed video. However, the processor 9 is able to process the raw uncompressed image data as well, to which end a volatile memory unit 11 is provided.

In other embodiments, the functionality of the components of the camera 5 is combined into fewer separate devices or distributed over more devices than are illustrated in FIG. 1.

The illustrated camera 5 is provided with user controls 12 and a display 13.

The camera 5 and the second camera system 2 are each configured to provide a data stream comprising a compressed video data stream and a metadata data stream. The compressed video data stream and the metadata data stream are provided with a common time base, so that metadata and compressed video are synchronized. In a particular embodiment, the metadata data stream and the compressed video data stream are provided in a multiplex.

A particular application is used here by way of example, in which the camera 5 is used to provide a compressed video data stream representing one or more persons in combination with a metadata data stream carrying information that either directly characterizes one or more biological processes in the persons represented or allows the video signal processing system 4 to derive such information. The camera 5 generates the metadata by first extracting one or more first signals, each representative of local temporal variations in either light intensity or color, or both, from a sequence of uncompressed images. Thus, the processes to be described herein are suitable for obtaining metadata on biological processes that cause a variation in the color or intensity of light reflected or passed through a living person. It is particularly used to obtain metadata on (quasi-) periodic biological processes such as heart beat and respiration. However, other phenomena, such as perspiration, can also be characterized, in particular by focusing on an appropriate range within the electromagnetic spectrum.

In one embodiment, to be described more fully herein, the camera 5 and the second camera system 2 provide only metadata directly representative of signals representative of local variations in at least one of light and color, meaning that such signals can be fully reconstructed from the metadata, or at least be reconstructed but for a phase difference. In another embodiment, the metadata is representative of parameter values directly characterizing the biological phenomenon. In this embodiment, signals representative of local variations in at least one of light and color on which the metadata is based can no longer be reconstructed from the metadata. Providing metadata representative of parameter values directly characterizing the biological phenomenon requires more intelligence in the camera 5 but it means that the size of the metadata is smaller. On the other hand, the video signal processing system 4 only has access to the biological information that the camera 5 has been programmed to provide (e.g. the heart rate values of the persons represented in the compressed video stream but not the respiration rate values). In addition, there must be a protocol to enable the video signal processing system 4 to determine the nature of the variable to which numerical values in the metadata relate.

The video signal processing system 4 can be implemented in the form of a general purpose computer. Thus, in FIG. 1, it is shown as comprising a network interface 6, central processing unit 15 (CPU) and main memory 16, user input device 17, mass-storage device 18 and graphics unit 19. It is connected to two display devices 20,21 by way of example. In an alternative embodiment a separate decoder device for decompressing the received compressed video stream can be provided, but in the illustrated embodiment this is done by the CPU 15 or the graphics unit 19. In the illustrated embodiment, the decompressed video can be shown on one of the display devices 20,21, and information relating to biological processes in living subjects represented in the video can be shown on the other. This display can be in the form of a graphical display including a graphical representation corresponding to the scene being shown in the video, with the biological information shown at screen positions corresponding substantially to the screen position at which the subject to which it relates is represented in the video. In an alternative embodiment, the biological information is overlaid on the video. In one embodiment, it is overlaid in response to input provided via the user input device 17. In a further embodiment, the video from the camera 5 and from the second camera system 2 can be shown on separate ones of the two display devices 20,21, e.g. to implement a surveillance system for security purposes. Biological information can be used to highlight scenes that are potentially of interest, e.g. those representing persons with elevated heart rates or perspiration.

Figure 2:
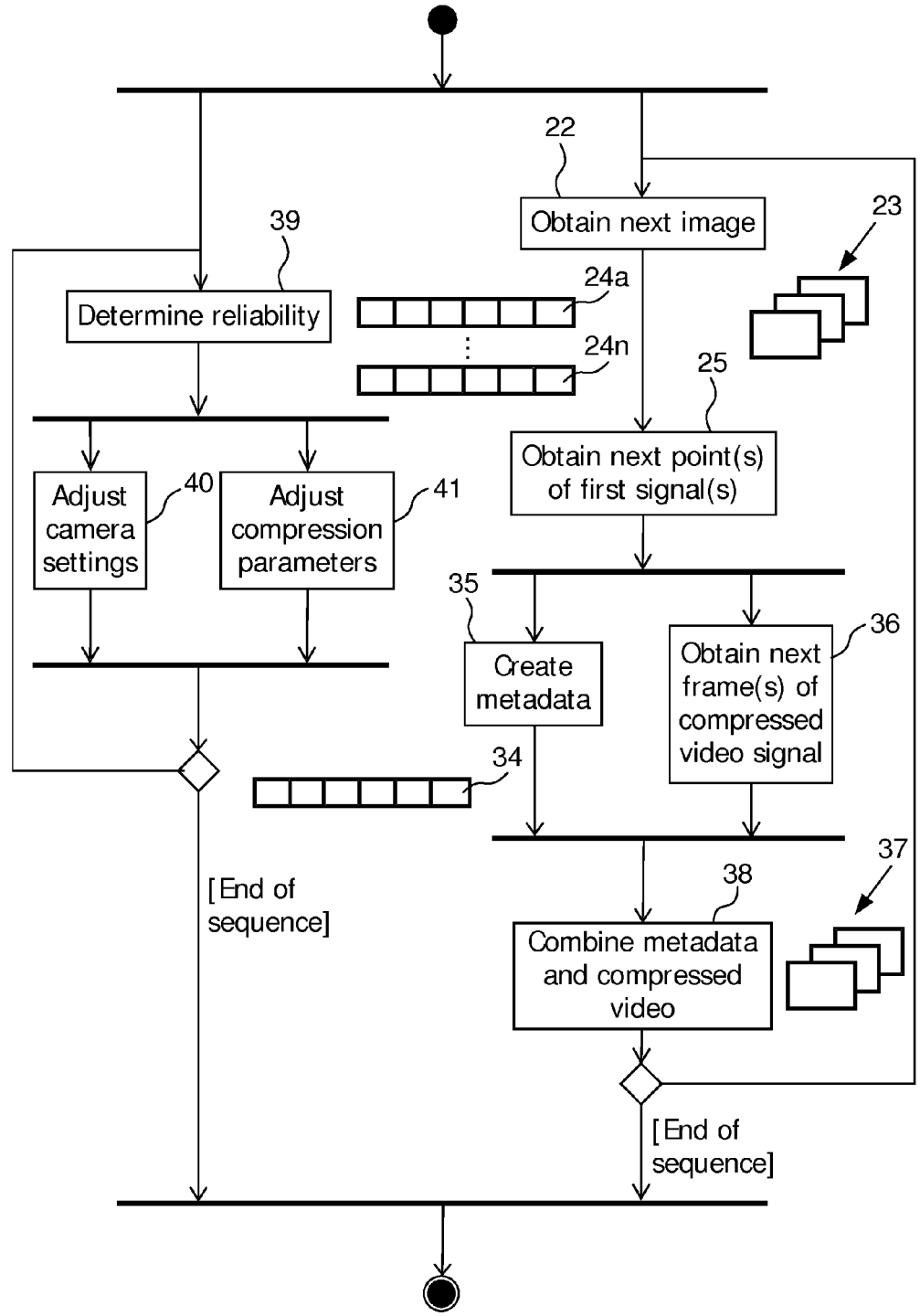
FIG. 2 is a flow chart illustrating some steps in a method carried out by the system for generating the signal.

Turning to FIG. 2, an example of a method of providing a combination of compressed video data and metadata as might be carried out by the processor 9 in the camera 5 will now be described.

With each obtained next image (step 22), a sub-sequence 23 of already obtained images is updated. In the illustrated embodiment, the next point in each of a set of first signals 24a-n is then obtained (step 25) using a remote photoplethysmographic method.

Figure 3:
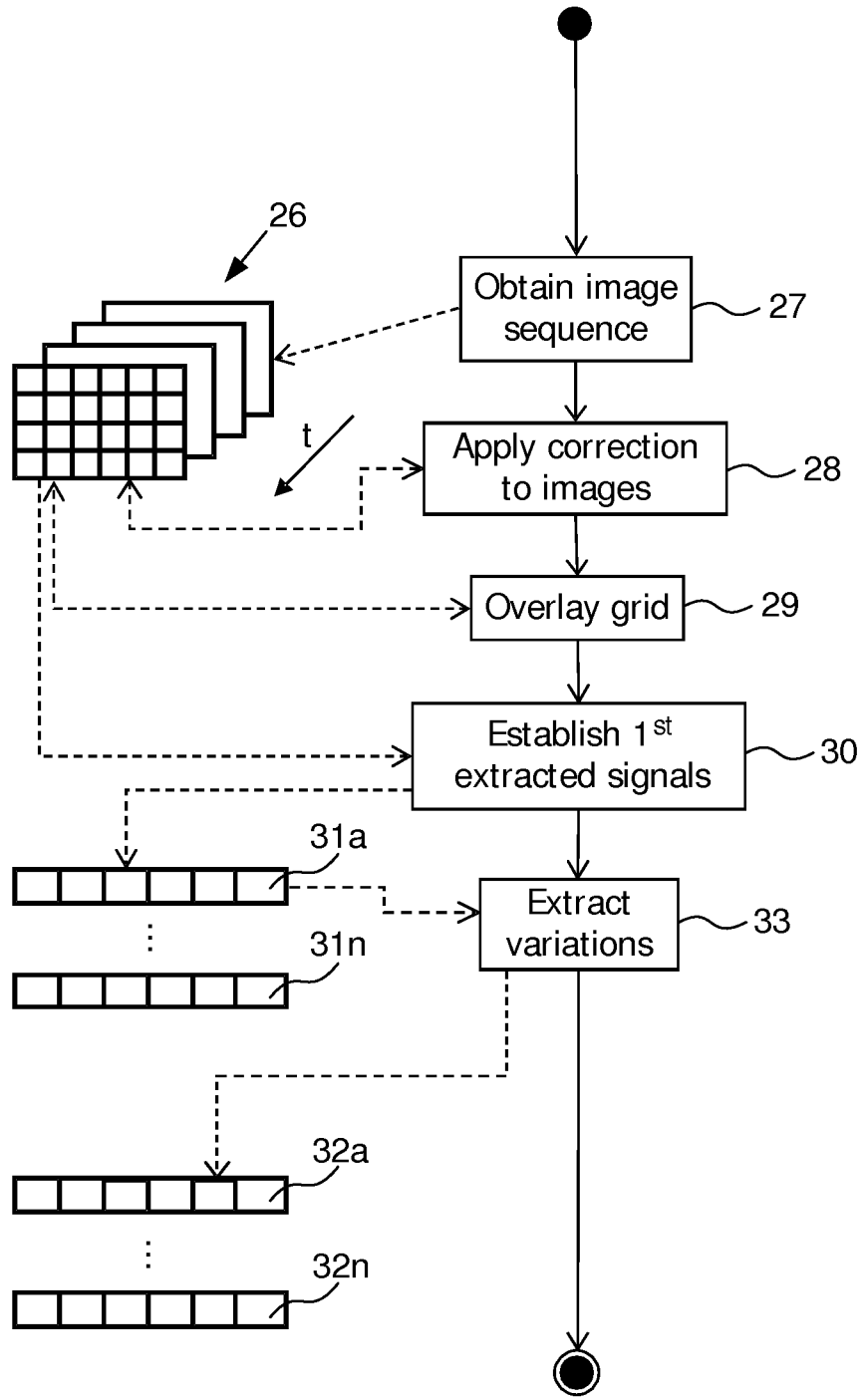
FIG. 3 is a flow chart illustrating in detail a step of generating signals representative of local temporal variations in at least one of intensity and color in a sequence of images as part of an embodiment of the method illustrated in FIG. 2.

One way in which first signals can be obtained is illustrated in outline in FIG. 3. A sequence 26 of images—this may be a combination of two or three sequences of images in different color channels—is obtained (step 27).

Then, in an optional but useful step, a correction is applied to the images 26. This can involve subtracting variations in overall light intensity levels (determined e.g. by averaging over all pixels in an image, indeed over all pixels of all corresponding image frames in different color channels) from the pixel values in the images. The aim is to remove variations due to background lighting or camera movement as much as possible, so as to isolate local variations in spatial regions of the images due to processes in the subjects represented in the images.

Then (step 29), a grid defining a plurality of measurement zones, each encompassing a plurality of pixel points, is laid over the images 26.

Next (step 30), a first set of extracted signals 31a-n is established, each value of an extracted signal 31a-n being based on a combination of pixel values from one of the measurement zones. This can be an average, for example. It can also be the mean value. It can also be a weighted average with different weights being used for pixel values from different color channels. Thus, for example, green can be over-weighted, because it is especially sensitive to variations in the level of oxyhaemoglobin in skin tissue. Similarly, blue can be given extra weight, because it is sensitive to variations in the water content of skin tissue and to variations in the moisture level of the skin surface, and thus representative of pulsating blood plasma flow and changing levels of perspiration. It is noted that, instead of carrying out spatial averaging, clustering can be carried out. That is to say, a signal or signal segment representative of intensity variations is generated for each of multiple pixel locations in a measurement zone, and these signals or signal segments are then clustered to generate a single extracted signal 31 for each measurement zone.

In the illustrated embodiment, a second set of signals 32a-n is generated (step 33). Each signal 32a-n is representative of variations in a corresponding one of the first set of signals 31. The second set of signals 32 can be generated by centering the signals 31 on their mean or average value. In alternative embodiments, a different or further technique for obtaining small signal variations is carried out, e.g. high-pass or band-pass filtering.

As illustrated, the signals 32a-n of the second set correspond to the first signals 24a-n. In other embodiments, a selection can be made. For example, those of the signals 32a-n of the second set with little or no information content can be discarded.

It is noted that an alternative embodiment (not shown in detail) is possible, in which the grid is not used. Instead, image segmentation is used to identify those parts of the images corresponding to living persons. Then, at least one measurement zone is selected within each region of interest. Regions of interest or measurement zones are tracked through the image sequence 26, and a signal is extracted from each measurement zone in the manner explained for the embodiment of FIG. 2. This embodiment is slightly more complicated, because the processor 9 in the camera 5 must be capable of carrying out the image segmentation, as well as algorithms for recognizing certain types of region of interest (e.g. a face recognition algorithm) and algorithms for tracking measurement zones and/or regions of interest through a sequence of images. However, where, for example, the second camera system 2 comprises a camera and a computing device, this embodiment could be feasible and would have the effect that fewer first signals 24a-n are generated, which are moreover all likely to be relevant to characterizing phenomena causing local variations in light intensity and/or color. An algorithm for face recognition is described in Viola, P. and Jones, M. J., "Robust real-time object detection", *Proc. IEEE Workshop on statistical and computational theories of vision*, 13 Jul. 2001. A tracking algorithm is described in De Haan et al., "True-motion estimation with 3-D recursive search block matching", *IEEE Transactions on circuits and systems for video technology*, 3 (5), October 1993, pp. 368-379.

After the step 25 (FIG. 2) of obtaining further points of the first signals 24a-n, new values in a stream 34 of metadata can be created (step 35). The metadata is in a pre-determined format, which can be proprietary or standardized.

As mentioned, in one embodiment, this step 35 entails further processing of the first signals 24a-n, or the sections thereof obtained thus far, in order to obtain values of parameters that directly characterize the phenomenon of interest. For example, the first signals 24a-n can be transformed into the frequency domain using a sliding window, in order to obtain a spectrum of each first signal at successive points in time. The value of the dominant frequency in at least a limited range of the spectrum is determined so as to obtain a time-varying signal representative of the heart rate or respiration rate, for example. These values can then be coded as metadata. In an embodiment, the values are associated with data identifying a spatial region in the images, so that the heart rate or respiration rate values can be associated with respective ones of several living beings represented in the sequence of images.

In the embodiment described herein in more detail, data directly representative of the first signals 24a-n are encoded into the metadata, together with associated data identifying the location of the measurement zone from which the first signal 24a-n concerned was extracted. The data identifying the location of the measurement zone may be implicit, e.g. in the order in which values are recorded in a table comprised in the metadata.

The image data of the images in the sub-sequence 23 obtained thus far are compressed (step 36) to obtain compressed video frames 37. In the illustrated embodiment of the method, at least one interframe compression technique is applied to the images in the sub-sequence 23 obtained thus far. Moreover, at least one lossy compression technique is used. Generally, such compression techniques will remove small-scale intensity and color variations. Thus, it will generally not be possible to extract signals representative of temporal variations in at least one of intensity and color caused by internal processes in a subject represented in the compressed video frames 37. For this reason, the extraction step 25 and compression step 36 are carried out in parallel on the obtained uncompressed images 23, or the extraction step 25 is carried out first.

The stream 34 of metadata and the compressed video frames 37 are multiplexed into a single data stream (step 38). Each is referred to a common time base, so that the first signals 24a-n or time-varying values of a parameter characterizing the internal process causing the temporal variations characterized by the first signals 24a-n are synchronized with the compressed video stream. Suitable formats for the combined data stream are provided by the MPEG-4 systems standard (ISO/IEC 14496-1), for example. The steps of the method illustrated in FIG. 2 and described above make up an independent and compete first embodiment of a method of providing a combination of compressed video data and metadata.

Certain additional features of a second embodiment that provide further effects are also illustrated in FIG. 2.

In this embodiment, a further step 39 is carried out that involves analysis of parts of the first signals 24a-n obtained thus far. In the illustrated embodiment, this step 39 is carried out whilst the compression (step 36) is ongoing, and also whilst the acquisition of images (step 22) is ongoing.

This is done because the outcome of the analysis is used to cause an adjustment of at least one parameter of a process of capturing the images (step 40) as well as to cause (step 41) an adaptation of at least one compression technique being applied (step 36) in parallel.

Various types of analysis and adaptation can be used. In one embodiment, the analysis is of the first signals 24a-n directly. In another embodiment, part or all of a process of deriving information from the first signals 24a-n that is characteristic of the internal process causing the local temporal variations in intensity and/or color is carried out, and the analysis is of the information derived in this way. For example, the analysis could be of the spectra of the first signals 24a-n.

In one embodiment, first signals 24a-n or values characterizing respective first signals 24a-n are compared to each other. Thus, it could be determined whether first signals 24a-n have a common dominant frequency to within a certain accuracy. In a sense, this is a determination of how many different persons are represented in the images. If there are several persons, then there is less scope for reducing the amount of metadata, so that the video compression rate will be increased. This ensures that the overall amount of data sent across the network 3 can stay within certain limits. If the dominant frequency is only present in first signals 24a-n associated with certain spatial regions of the images, then the compression can be lower in those regions than in other regions. This is because they are likely to be the most interesting regions to a human observer. In case of human subjects, these regions are likely to correspond to persons' bodies. If the dominant frequency changes rapidly in time, then an interframe compression technique can be adapted to use less prediction, because there are likely to be many changes in the scene represented by the images 23, e.g. persons coming and going.

As far as the analysis in combination with the adjustment of parameters of the process of capturing the images 23 is concerned, these include parameters corresponding to settings of at least one of the image sensor array 7 and the optical system 8 that is used to focus light onto the image sensor array 7. This means in particular that certain parts of the scene can be captured with a higher resolution, even though the pixel count of the image sensor array 7 may be quite low. The relevant analysis can be a determination of the signal-to-noise ratio and/or of the dynamic range of the first signals 24a-n, for example. If the signal-to-noise ratio is low, then the camera 5 can zoom in. If the dynamic range is low, then the quantization step of an analogue-to-digital converter in the image sensor array 7 can be made smaller, for example. Further possible analyses include a determination of the consistency of the dominant frequency o the first signals 24a-n corresponding to the frequency of a biological phenomenon of interest (heart rate, respiration rate) or a determination of the frequency distributions of transformations to the frequency domain of the first signals 24a-n.

By adapting the image capturing process and/or the compression in this way, there is implemented a closed feedback loop between the camera 5 hardware used to capture images and a detector of biometric signals. Control parameters of the camera 5 are adjusted continuously and automatically in order to keep the reliability of the detected biometrical signals at a constant high level.

Figure 4:
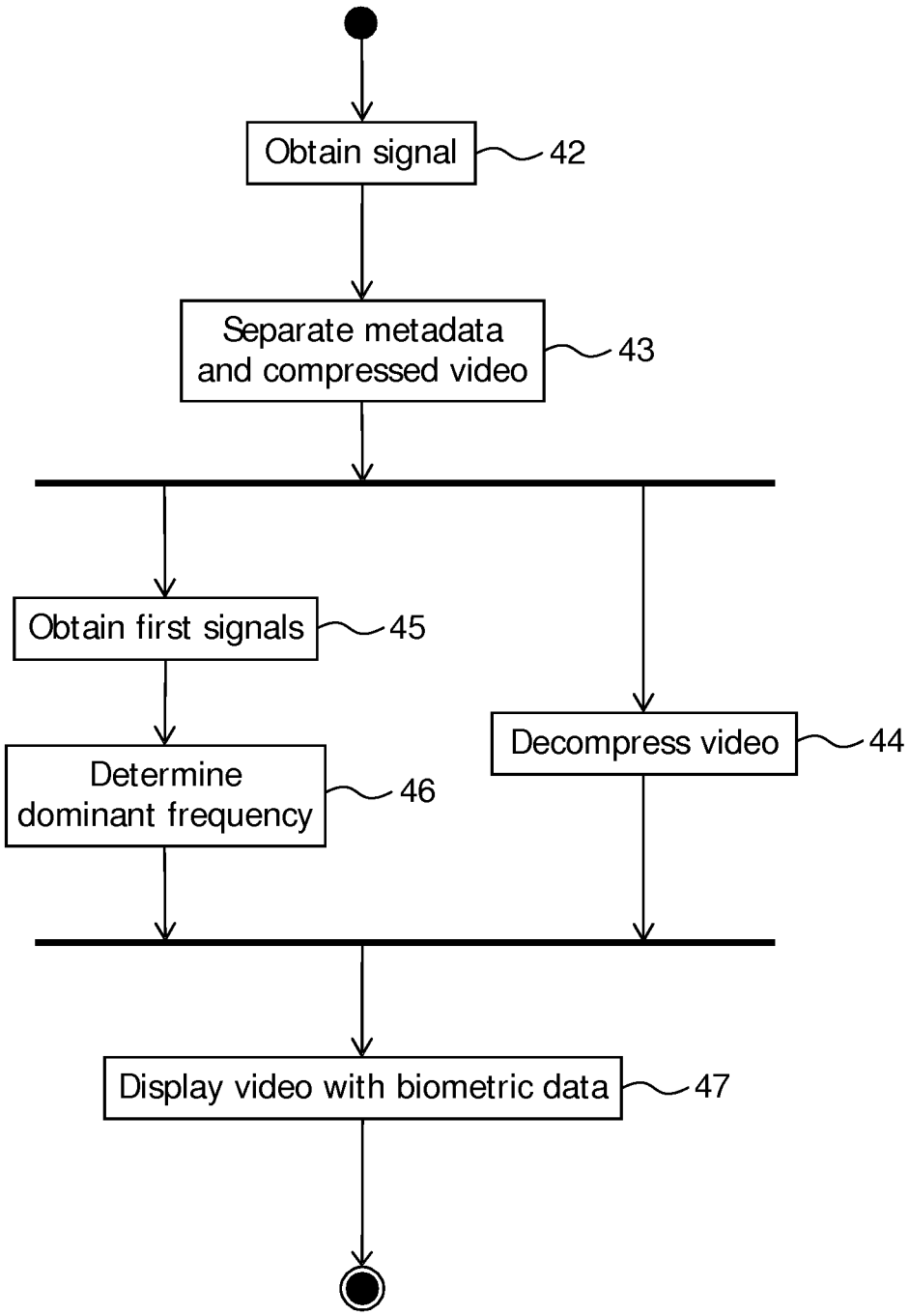
FIG. 4 is a flow chart giving an outline of a first method of processing the combined signal.
Figure 5:
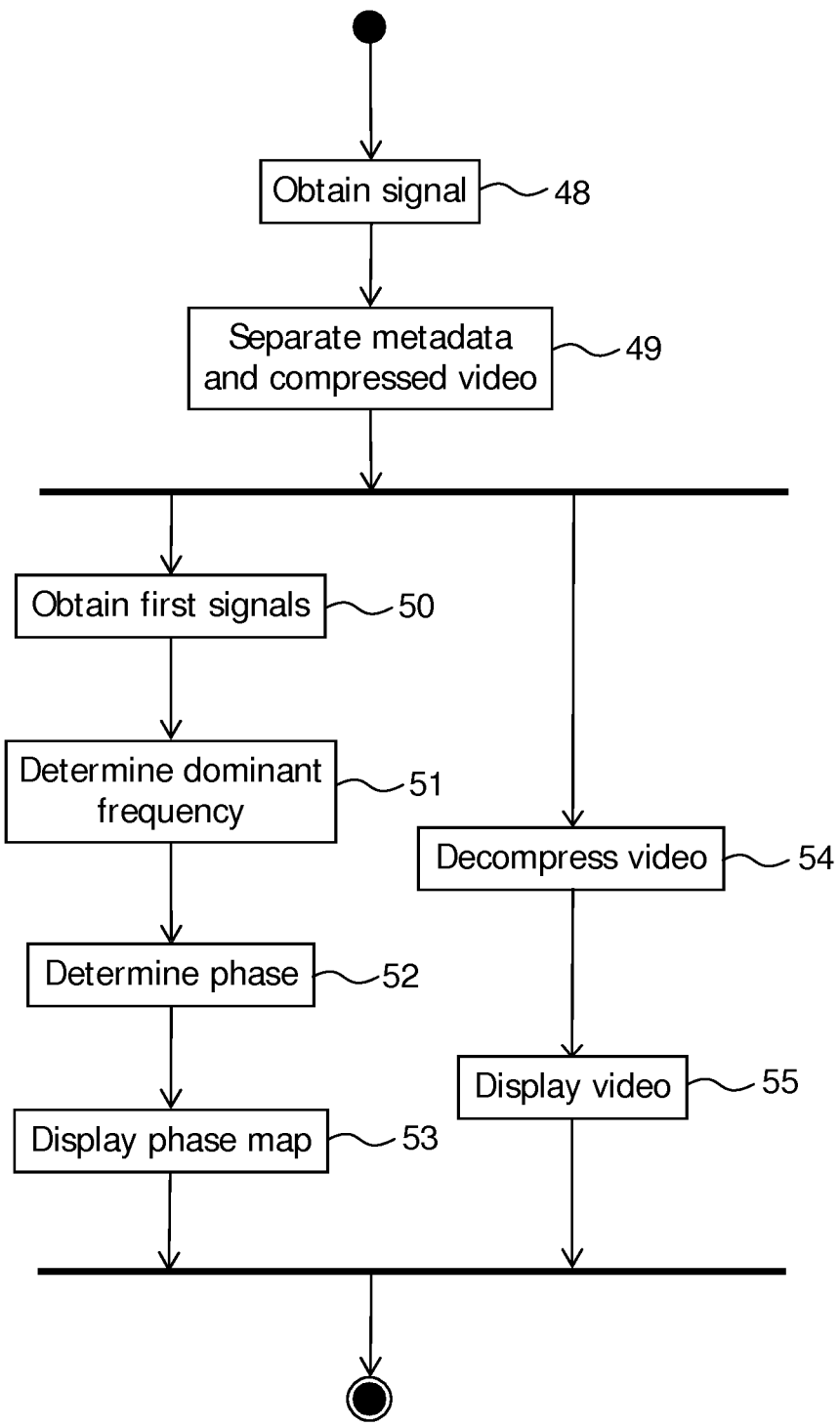
FIG. 5 is a flow chart giving an outline of a second method of processing the combined signal.

In the example in which at least some of the first signals 24a-n are directly encoded as metadata, the video signal processing system 4 can carry out a method as illustrated in FIG. 4 or a method as illustrated in FIG. 5.

In the method illustrated in FIG. 4, the video signal processing system 4 receives the multiplex (step 42), and separates the metadata from the compressed video stream (step 43). The compressed video stream is decompressed (step 44).

From the metadata, the video signal processing system 4 determines the first signals 24a-n (step 45) together with associated information identifying the spatial location in the images with which the first signals 24a-n are associated. A frequency transform (step 46) is applied to determine the dominant frequency in at least a limited range of the spectrum of each first signal 24a-n. This is done repeatedly, using a sliding window, so that the development of the dominant frequency over time can be tracked. In particular, values of the dominant frequency can be associated with points in time corresponding to points in the decompressed video sequence obtained in the parallel step 44. Thus, the frequency information and the decompressed video can be displayed together (step 47) on one of the display devices 20,21. In one embodiment, locations of living subjects represented in the decompressed video within the display area are determined. Values of at least one parameter characterizing a biological phenomenon are determined for each such person based on the information extracted from the metadata, and displayed overlaid on the decompressed video with a visible link to the location at which the person is represented. In another embodiment, alerts are provided whenever values of a parameter characterizing an internal process in a subject represented in the decompressed video meet certain criteria. Thus, for example, an audible or visible alert can be provided whenever the video shows a person whose heart rate values meet certain criteria, e.g. criteria indicative of a medical problem or of a security risk.

FIG. 5 shows a similar method of processing a signal including a combination of compressed video data and metadata, in particular metadata directly representative of a plurality of first signals 24a-n representative of local variations in at least one of intensity and color. The metadata enables a determination of an associated image location to be made for each first signal 24a-n. Thus, the video signal processing system 4 is able to process each first signal 24a-n to determine at least one associated value of a parameter characterizing the signal, and then generate a map of these parameter values.

In the illustrated example, the multiplex comprising the first signals 24a-n in the form of a metadata stream 34 and the compressed video stream is obtained (step 48). The metadata stream 34 is separated from the compressed video stream (step 49). Then, the first signals 24a-n and the associated information linking each of them to a location in an image area are obtained 50. The first signals 24a-n are each analyzed to determine the dominant frequency within at least a limited range of their spectrum (step 51). Then, in the illustrated embodiment, the phase at the dominant frequency is determined for each first signal 24a-n (step 52). In the illustrated embodiment, this information is used to generate a phase map (step 53). In parallel, the compressed video stream is decompressed (step 54), and the decompressed video is also displayed (step 55). For example, the phase map can be displayed on one of the first and second display devices 20,21, and the decompressed video can be displayed on the other.

In an alternative embodiment, one of the decompressed video and the phase map is used to enhance the display of the other. Thus, for example, where the grid defining the measurement zones in the method of FIG. 3 is relatively coarse, image segmentation carried out on the decompressed video can be used to enhance the image provided by the phase map.

It is noted that, in the alternative in which the metadata provided to the video signal processing system 4 no longer corresponds directly to the first signals 24a-n, one or both of the first and second camera systems 1,2 can perform a method according to FIG. 4 or 5 subsequent to the method of FIG. 3, so that the metadata stream 34 will carry data representative of the dominant frequency within at least a limited range of the spectrum of each of the first signals 24a-n, or will carry the information representative of a phase map. In either case, additional information enabling internal processes in each of a number of subjects represented in images captured by a camera to be characterized is provided.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

In an embodiment, instead of providing the first signals 24a-n in the time domain, information representative of a transformation of the first signals 24a-n into the temporal frequency domain is provided in the metadata stream 34.

The invention claimed is:

1. A method of providing a combination of video data and metadata comprising the acts of:
   obtaining a sequence of images captured by a video camera, the sequence of images including subject images of at least one subject;
   extracting at least one signal from at least part of the sequence of images representing the subject images,
   wherein each of the at least one extracted signal characterizes local temporal variations in at least one of light intensity and color of light captured from the at least one subject represented in the at least part of the sequence of images;
   generating metadata (i) based on the at least one extracted signal that characterizes local temporal variations in at least one of light intensity and color of the at least one subject represented in the at least part of the sequence of images, (ii) for characterizing at least one biometric process in the at least one subject represented in the at least part of the sequence of images, wherein the biometric process causes the local temporal variations in at least one of color and intensity of light captured from the at least one subject;
   applying at least one video compression technique on image data of images from the sequence to obtain compressed video data,
   wherein the at least one extracted signal is extracted from images in a state prior to the application of the at least one compression technique to image data from those images; and
   providing the compressed video data with the generated metadata.

2. The method according to claim 1, further comprising the act of adapting the application of the at least one compression technique in dependence on an outcome of an analysis of data at least based on obtained parts of at least one of the at least one extracted signal.

3. The method according to claim 1, further comprising the act of, whilst obtaining the sequence of images, causing adjustments of parameters corresponding to settings of at least one of an image sensor array and an optical system in a process of capturing the images using at least one camera in dependence on an outcome of an analysis of data at least based on obtained parts of at least one of the extracted signals.

4. The method according to claim 1, wherein the method is carried out by a processing system included in a camera.

5. The method according to claim 1, wherein the generated metadata includes at least one signal characterizing local temporal variations in at least one of light intensity and color in the sequence of images.

6. A system for providing a combination of video data and metadata, comprising:
   at least an interface to a camera for capturing a sequence of images, the sequence of images including subject images of at least one subject;
   video data processing system, configured to:
   apply at least one video compression technique on image data of images from the sequence to obtain compressed video data, extract at least one signal from at least part of the sequence of images representing the subject images, each of the at least one extracted signal characterizing local temporal variations in at least one of light intensity and color of light captured from the at least one subject represented in the at least part of the sequence of images; and generate metadata (i) based on the at least one extracted signal that characterizes local temporal variations in at least one of light intensity and color of the at least one subject represented in the at least part of the sequence of images, (ii) for characterizing at least one biometric process in the at least one subject represented in at least part of the images, wherein the biometric process causes the local temporal variations in at least one of color and intensity of light captured from the at least one subject, wherein the at least one extracted signal is extracted from images in a state prior to the application of the at least one compression technique to image data from those images; and an output interface for providing the compressed video data with the generated metadata.

7. A method of processing a signal comprising the acts of:

obtaining a signal that comprises a combination of compressed video and generated metadata, wherein the compressed video is obtainable by applying at least one video compression technique on image data of images from a sequence of images, the sequence of images including subject images of at least one subject, and wherein the generated metadata includes at least one signal characterizing local temporal variations in at least one of light intensity and color of light captured from the at least one subject represented in the at least part of the sequence of images, wherein the generated metadata is based on at least one signal extracted from at least part of the sequence of images, prior to application of the at least one video compression technique on the image data of images from the sequence of images, that characterizes the local temporal variations in at least one of light intensity and color of the at least one subject represented in the at least part of the sequence of images; and calculating at least one value of a parameter characterizing at least one biometric process in the at least one subject represented in the at least part of the sequence of images, wherein the biometric process causes the local temporal variations in at least one of color and intensity of light captured from the at least one subject, using as input at least one of the signals of the generated metadata characterizing local temporal variations in at least one of light intensity and color in the sequence of images.

8. A system for processing a signal that includes a combination of compressed video and metadata, comprising:

an interface for obtaining a signal that comprises a combination of compressed video and generated metadata, wherein the compressed video is obtainable by applying at least one video compression technique on image data of images from a sequence of images, the sequence of images including subject images of at least one subject, and wherein the generated metadata includes at least one signal characterizing local temporal variations in at least one of light intensity and color of light captured from the at least one subject represented in the at least part of the sequence of images, wherein the generated metadata is based on at least one signal extracted from at least part of the sequence of images, prior to application of the at least one video compression technique on the image data of images from the sequence of images, that characterizes local temporal variations in at least one of light intensity and color of the at least one subject represented in the at least part of the sequence of images; and a data processing system for calculating at least one value of a parameter characterizing at least one biometric process in the at least one subject represented in the at least part of the sequence of images, wherein the process causes the local temporal variations in at least one of color and intensity of light captured from the at least one subject, using as input at least one of the signals of the generated metadata characterizing local temporal variations in at least one of light intensity and color in the sequence of images.

9. A non-transitory computer readable medium embodied with a computer program including a set of instructions, executable by a processor for causing the processor to perform act of:

obtaining a sequence of images captured by a video camera, the sequence of images including subject images of at least one subject;

extracting at least one signal from at least part of the sequence of images representing the subject images, wherein each of the at least one extracted signal characterizes local temporal variations in at least one of light intensity and color of light captured from the at least one subject represented in the at least part of the sequence of images;

generating metadata (i) based on the at least one extracted signal that characterizes local temporal variations in at least one of light intensity and color of the at least one subject represented in the at least part of the sequence of images, (ii) for characterizing at least one biometric process in the at least one subject represented in the at least part of the sequence of images, wherein the biometric process causes the local temporal variations in at least one of color and intensity of light captured from the at least one subject;

applying at least one video compression technique on image data of images from the sequence to obtain compressed video data, wherein the at least one extracted signal is extracted from images in a state prior to the application of the at least one compression technique to image data from those images; and providing the compressed video data with the generated metadata.

10. A device comprising:

at least an interface to a camera for capturing a sequence of images, the sequence of images including subject images of at least one subject; and a processor configured to:

apply at least one video compression technique on image data of images from the sequence to obtain compressed video data, extract at least one signal from at least part of the sequence of images representing the subject images, each of the at least one extracted signal characterizing local temporal variations in at least one of light intensity and color of light captured from the at least one subject represented in the at least part of the sequence of images; and generate metadata (i) based on the at least one extracted signal that characterizes local temporal variations in at least one of light intensity and color of the at least one subject represented in the at least part of the sequence of images, (ii) for characterizing at least one biometric process in the at least one subject represented in at least part of the images, wherein the biometric process causes the local temporal variations in at least one of color and intensity of light captured from the at least one subject, wherein the at least one extracted signal is extracted from images in a state prior to the application of the at least one compression technique to image data from those images; and an output interface for providing the compressed video data with the generated metadata.

11. The device of claim 10, wherein the subject images include a plurality of subjects, and wherein the processor is further configured to:

extract a plurality of signals corresponding to the plurality of subjects from at least part of the sequence of images representing the subject images, and generate metadata based on the plurality extracted signals for characterizing a biometric process for each of the plurality of subjects in the sequence of images.

12. The device of claim 10, wherein the processor is further configured to:

determine where at least one face of the at least one subject is in the sequence of images, and encode spatial parts of the sequence of images including the at least one face in greater detail than remaining parts of the sequence of images.

13. The device of claim 10, wherein the processor is further configured to:

adjust parameters of the camera to increase capture of components of the at least one extracted signal carrying information relating to the at least one biometric process in the at least one subject, including capturing more information from a first part of the sequence of images than a second part of the sequence of images.

14. The device of claim 13, wherein the first part includes a face of the at least one subject.

15. A device comprising:

an interface for obtaining a signal that comprises a combination of compressed video and generated metadata, wherein the compressed video is obtainable by applying at least one video compression technique on image data of images from a sequence of images, the sequence of images including subject images of at least one subject, and wherein the generated metadata includes at least one signal characterizing local temporal variations in at least one of light intensity and color of light captured from the at least one subject represented in the at least part of the sequence of images, wherein the generated metadata is based on at least one signal extracted from at least part of the sequence of images, prior to application of the at least one video compression technique on the image data of images from the sequence of images, that characterizes local temporal variations in at least one of light intensity and color of the at least one subject represented in the at least part of the sequence of images; and a processor configured to calculate at least one value of a parameter characterizing at least one biometric process in the at least one subject represented in the at least part of the sequence of images, wherein the process causes the local temporal variations in at least one of color and intensity of light captured from the at least one subject, using as input at least one of the signals of the generated metadata characterizing local temporal variations in at least one of light intensity and color in the sequence of images.

16. The device of claim 15, wherein the subject images include a plurality of subjects, and wherein the processor is further configured to:

extract a plurality of signals corresponding to the plurality of subjects from at least part of the sequence of images representing the subject images, and generate metadata based on the plurality extracted signals for characterizing a biometric process for each of the plurality of subjects in the sequence of images.

17. The device of claim 15, wherein the processor is further configured to:

determine where at least one face of the at least one subject is in the sequence of images, and encode spatial parts of the sequence of images including the at least one face in greater detail than remaining parts of the sequence of images.

18. The device of claim 15, wherein the processor is further configured to:

adjust parameters of the camera to increase capture of components of the at least one extracted signal carrying information relating to the at least one biometric process in the at least one subject, including capturing more information from a first part of the sequence of images than a second part of the sequence of images.

19. The device of claim 18, wherein the first part includes a face of the at least one subject.

* * * * *